United States Patent
Keppner

(10) Patent No.: US 11,583,879 B2
(45) Date of Patent: Feb. 21, 2023

(54) DISPENSER FOR APPLYING LIQUID, IN PARTICULAR FOR APPLYING A PHARMACEUTICAL LIQUID, AND SET COMPRISING SUCH A DISPENSER

(71) Applicant: Aptar Radolfzell GmbH, Radolfzell (DE)

(72) Inventor: Frank Keppner, Albstadt (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 17/423,607

(22) PCT Filed: Dec. 11, 2019

(86) PCT No.: PCT/EP2019/084741
§ 371 (c)(1),
(2) Date: Jul. 16, 2021

(87) PCT Pub. No.: WO2020/148032
PCT Pub. Date: Jul. 23, 2020

(65) Prior Publication Data
US 2022/0097087 A1   Mar. 31, 2022

(30) Foreign Application Priority Data
Jan. 17, 2019   (EP) .................................... 19152388

(51) Int. Cl.
*B05B 11/04*   (2006.01)
*B05B 11/00*   (2023.01)

(52) U.S. Cl.
CPC ........ *B05B 11/047* (2013.01); *B05B 11/0039* (2018.08); *B05B 11/3087* (2013.01); *B05B 11/048* (2013.01)

(58) Field of Classification Search
CPC .............. B05B 11/047; B05B 11/0039; B05B 11/3087; B05B 11/048; B05B 11/308;
(Continued)

(56) References Cited

U.S. PATENT DOCUMENTS

| | | |
|---|---|---|
| 4,014,797 A | 3/1977 | Raines et al. |
| 5,289,952 A | 3/1994 | Gueret |

(Continued)

FOREIGN PATENT DOCUMENTS

| | | |
|---|---|---|
| CN | 1195301 A | 10/1998 |
| CN | 1860349 A | 11/2006 |

(Continued)

OTHER PUBLICATIONS

Japanese Office Action with English translation issued in corresponding Japanese Application No. 2021-539034 dated Jul. 5, 2022 (14 pages).

(Continued)

*Primary Examiner* — Vishal Pancholi
(74) *Attorney, Agent, or Firm* — Flynn Thiel, P.C.

(57) ABSTRACT

A dispenser for applying liquid, having a housing with an applicator opening and a liquid reservoir. The dispenser has a ventilation duct by which an ambient atmosphere is connected to the liquid reservoir so that, after the application of liquid, an inflow of air from the atmosphere is permitted into the liquid reservoir. The dispenser is provided with a detection installation which for detecting an application procedure detects air flowing in through the ventilation duct. The dispenser has a protective cap covering the applicator opening on the housing. The dispenser in the ventilation duct has a switch valve operable by activating a push-button on the external side of the housing. The protective cap acts on (Continued)

the push-button when placed on the housing or when the protective cap is being placed thereon to open the switch valve.

16 Claims, 4 Drawing Sheets

(58) Field of Classification Search
CPC ............ B05B 11/0067; B05B 11/0032; B05B 11/0002; B05B 11/0044; A61M 2205/502; A61M 11/008; A61M 15/0025; A61M 15/008
See application file for complete search history.

(56) References Cited

U.S. PATENT DOCUMENTS

| | | | |
|---|---|---|---|
| 5,798,041 | A | 8/1998 | Zuk, Jr. |
| 7,373,816 | B2 | 5/2008 | Strohrmann et al. |
| 7,614,504 | B2 | 11/2009 | South et al. |
| 7,781,707 | B2 | 8/2010 | Enrietti |
| 7,892,592 | B1 | 2/2011 | Chen et al. |
| 10,821,241 | B2 | 11/2020 | Kohnle et al. |
| 2013/0037575 | A1* | 2/2013 | van der Molen ... B05B 11/3087 222/207 |
| 2014/0077000 | A1* | 3/2014 | Cooper ............... B05B 7/2489 239/302 |
| 2014/0228783 | A1 | 8/2014 | Kraft |
| 2016/0193615 | A1* | 7/2016 | Schmid ............... B05B 12/087 222/1 |
| 2017/0102256 | A1 | 4/2017 | Sosna et al. |
| 2018/0180455 | A1 | 6/2018 | Nakao et al. |
| 2018/0264491 | A1* | 9/2018 | Goldowsky ........... B01L 3/0293 |
| 2019/0366020 | A1 | 12/2019 | Tritschler et al. |

FOREIGN PATENT DOCUMENTS

| | | |
|---|---|---|
| CN | 1964831 A | 5/2007 |
| CN | 101184544 A | 5/2008 |
| CN | 102967335 A | 3/2013 |
| CN | 103334859 A | 10/2013 |
| CN | 105517609 A | 4/2016 |
| CN | 106537100 A | 3/2017 |
| EP | 0511894 A1 | 11/1992 |
| EP | 2708289 A2 | 3/2014 |
| EP | 3043156 A1 | 7/2016 |
| EP | 3321646 A1 | 5/2018 |
| EP | 3376182 A1 | 9/2018 |
| FR | 2972995 A1 | 9/2012 |
| GB | 726335 | 3/1955 |
| JP | 862011 A | 3/1996 |
| JP | 200046609 A | 2/2000 |
| JP | 2003276719 A | 10/2003 |
| JP | 2009240898 A | 10/2009 |
| JP | 201765759 A | 4/2017 |
| JP | 2017129470 A | 7/2017 |
| JP | 3213184 U | 10/2017 |
| JP | 2018514257 A | 6/2018 |
| WO | 2011115484 A1 | 9/2011 |
| WO | 2015194962 A1 | 12/2015 |
| WO | 2018165326 A1 | 9/2018 |

OTHER PUBLICATIONS

Chinese Office Action issued in corresponding Chinese Application No. 201980089427.4, dated May 19, 2022 (10 pages).
International Search Report with English Translation issued in corresponding International Application No. PCT/EP2019/084741 dated Feb. 24, 2020 (6 pages).
Written Opinion of International Searching Authority issued in corresponding International Application No. PCT/EP2019/084741 dated Feb. 24, 2020 (8 pages).
Chinese Office Action issued in corresponding Chinese Application No. 2022042102168960 dated Apr. 25, 2022 (12 pages).

* cited by examiner

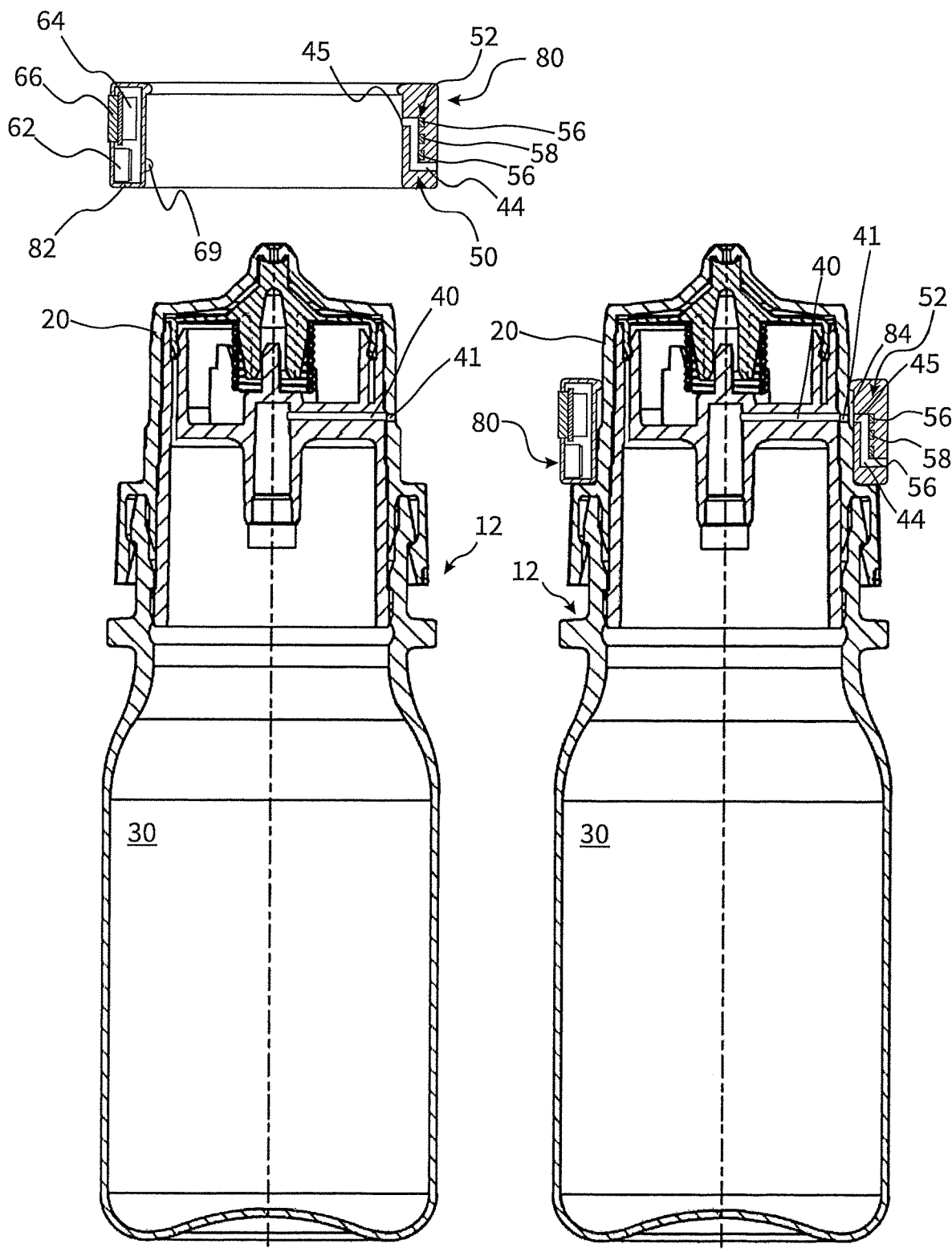
*Fig. 4A*　　　　*Fig. 4B*

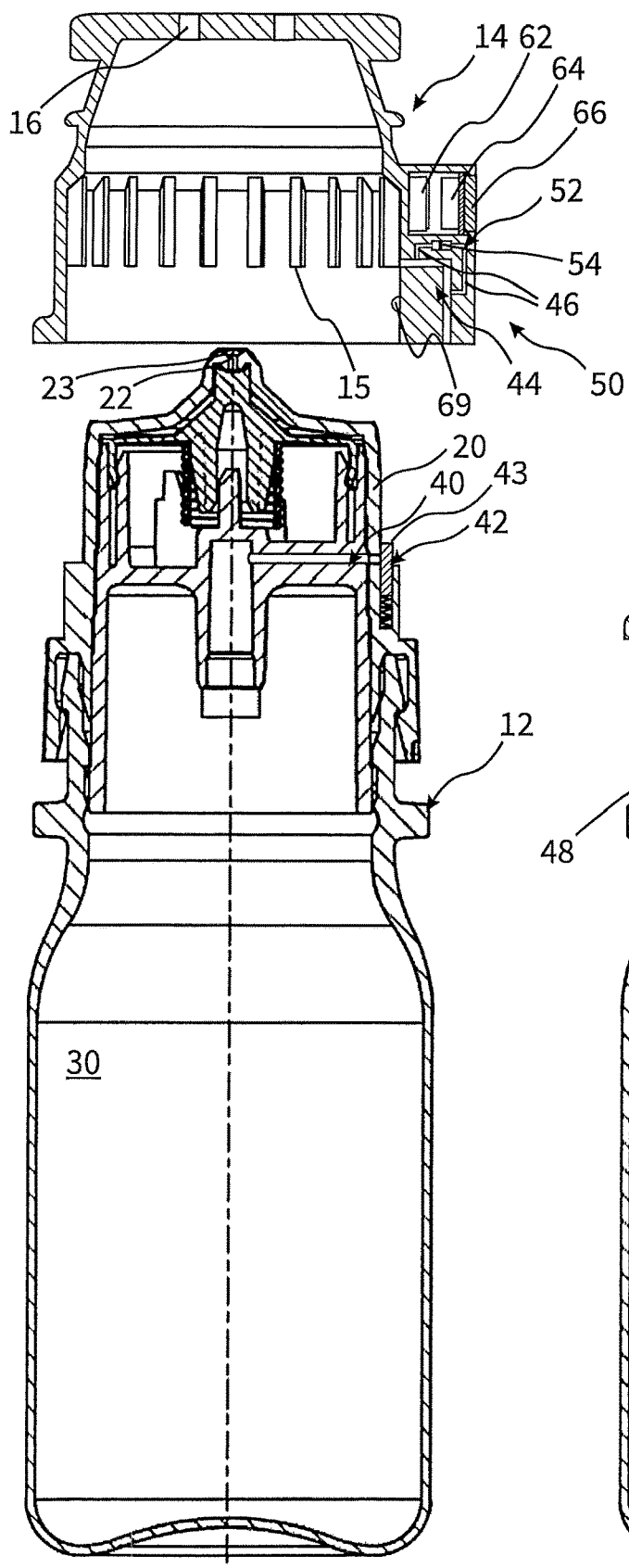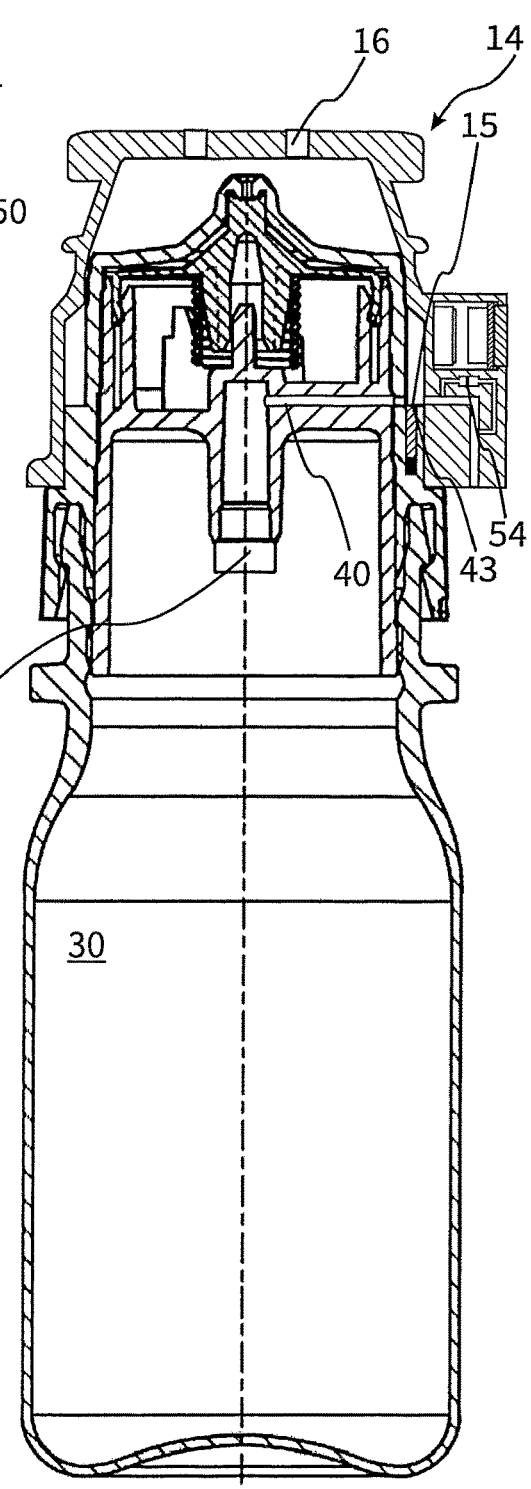
Fig. 5A                    Fig. 5B

DISPENSER FOR APPLYING LIQUID, IN PARTICULAR FOR APPLYING A PHARMACEUTICAL LIQUID, AND SET COMPRISING SUCH A DISPENSER

FIELD OF APPLICATION

The invention relates to a dispenser for applying liquid, in particular for applying a pharmaceutical liquid, and to a set comprising such a dispenser.

BACKGROUND OF THE INVENTION

A dispenser of the generic type possesses a housing having an applicator opening through which liquid from a liquid reservoir of the dispenser can be delivered. This can take place, for example, in that the liquid reservoir is configured as a squeeze bottle and is manually compressed for the purpose of the application.

As a result of the application, a negative pressure by virtue of the dispensed liquid volume leaving the liquid reservoir is generated in the liquid reservoir in dispensers of the generic type. In order for this liquid volume to be compensated, the dispenser has a ventilation duct by way of which air can be inducted into the liquid reservoir. For the purpose of the avoidance of contamination, the ventilation duct can be provided with a filter assembly.

Depending on the design embodiment of such a dispenser, the dispenser can be configured for applying a dose of liquid per activation, or for applying a quantity of liquid which can be freely determined by the type of activation by the user.

In a dispenser of the generic type, it can be desirable for the applied quantity of liquid, or the number of applied doses of liquid, to be detected, in particular by electronic measuring means. This can be desirable both in the typical operation of such a dispenser at the end-user or else in a trial phase by special product testers. The purpose may be, for example, to estimate the residual quantity of liquid in the liquid reservoir, or to enable the user to be reminded when an envisaged application has not been performed.

Diverse measuring systems for liquid dispensers in which the activation per se is detected and processed in particular in the form of counting are already known from the prior art. However, in such systems it is not guaranteed in every case that a correct application has actually been performed, for example an incorrect application can happen when the dispenser when activated was not aligned according to the intended use.

It has likewise already been considered to detect the flow of liquid per se, thus to add a sensor to a suitable measuring installation in an applicator duct between the liquid reservoir and the applicator opening. This however is often difficult to implement in terms of construction and leads to a substantial change in the construction of a dispenser. Depending on the materials used in a corresponding sensor system, the contact between the liquid and this sensor system is also disadvantageous in terms of the sensor system and/or the liquid.

OBJECT AND ACHIEVEMENT

It is an object of an embodiment of the invention to provide a dispenser which in an advantageous manner permits the detection of the liquid application and herein avoids or minimizes the above-mentioned issues of the prior art.

Proposed according to an embodiment of the invention to this end is a dispenser for applying liquid, in particular for applying a pharmaceutical liquid.

In accordance with dispensers of the generic type, such dispensers according to an embodiment of the invention have a housing having an applicator opening for applying liquid, and a liquid reservoir for storing the liquid prior to the application. The dispensers according to the liquid are portable dispensers for the end-user and in particular for patients, hereunder collectively referred to as users. The maximum volume of the liquid reservoir therefore is usually between 5 ml and 500 ml, in particular between 5 ml and 50 ml.

Upon activation by the user, the liquid in the liquid reservoir is conveyed through an applicator duct to the applicator opening. An outlet valve which only opens upon reaching a defined threshold pressure is preferably disposed upstream of the applicator opening. The form of application can in particular be that of a liquid flow, an atomized spray jet mixed with air, or the form of individual drops. In the case of a drop dispenser, the applicator opening is surrounded by a drop-forming surface to which the liquid to be delivered adheres until the quantity of liquid is sufficiently large to be released in the form of drops from the drop-forming surface. The drop-forming surface externally is preferably delimited by a tear-off edge, so as to guarantee a particularly uniform size of drop.

A manually activatable pump installation, having a pump chamber and pump valves on the input side and the output side can in particular be provided for conveying the liquid from the liquid reservoir to the applicator opening. A particularly substantial alternative thereto is the design of the dispenser as a squeeze-bottle dispenser. In this case, the liquid reservoir, or a surrounding activation member, is elastically compressible so that a positive pressure which causes conveying in the direction of the applicator opening is generated in the liquid.

In a dispenser according to an embodiment of the invention, upon completing an application and when resetting the liquid reservoir or the surrounding activation member, air from the environment is inducted into the liquid reservoir so as to compensate for the previously applied liquid volume and to adapt the pressure in the liquid reservoir to the ambient pressure again.

For this purpose, a dispenser according to an embodiment of the invention possesses a ventilation duct by which an ambient atmosphere is connected to the liquid reservoir so as to, after the application of liquid, permit an inflow of air from the atmosphere.

According to the main aspect of an embodiment of the invention, the dispenser furthermore possesses a detection installation for detecting an application procedure, wherein the detection installation is configured for detecting the air flowing in through the ventilation duct.

According to the main aspect of an embodiment of the invention it is accordingly proposed that neither the activation of the dispenser nor a direct detection of the applied liquid volume is utilized for detecting the application, but instead the ventilation procedure which follows the application and in the context of which air, in particular from an ambient atmosphere, flows into the liquid reservoir or a surrounding activation member.

It has been demonstrated that an application can be reliably identified herewith, wherein only the performance of the application per se or else the applied liquid is able to be indirectly detected, depending on the design embodiment. Contact between the liquid and a corresponding sensor system can be avoided here. Any activation of the dispenser which has not led to an application of liquid, and therefore also does not lead to an inflow of air, correctly does not result in a detection.

A detection installation in the most general form is a mechanism which varies the state thereof in a reproducible manner when an event, presently the introduction of air, takes place. While purely mechanical construction modes appear to be conceivable here, an electronic detection installation is preferably provided in a dispenser according to an embodiment of the invention including a detection installation having a sensor and a memory, such that as a consequence of the application procedure detected indirectly by sensors changing the state of the memory. A sensor according to an embodiment of the invention is disposed in or on the periphery of the ventilation duct and directly detects the air flow directed thereby into the liquid reservoir, and thus indirectly the previously performed application of liquid.

Various sensors can be considered for detecting the inflow of air.

The detection installation can thus have a sensor assembly for detecting the air flowing in through the ventilation duct, the sensor assembly being configured for detecting a differential pressure between two locationally spaced apart reference points of the ventilation duct. This can take place in particular in that a bypass piece which is closed off by a deflectable surface portion is provided in the ventilation duct or a particular part thereof (measuring duct). This membrane is deflected as a function of the differential pressure, which can be electronically detected. A deflectable surface portion can also directly form a wall part of the ventilation duct and can be deflected as a function of the pressure prevailing therein. A further design which can be utilized in the context of an embodiment of the invention provides that the sensor assembly comprises at least two temperature sensors and at least one heating element which are disposed in the ventilation duct, wherein the two temperature sensors are provided upstream and downstream of the heating element. The detection installation can draw a conclusion pertaining to the quantity of inflowing air from the temperature difference of the temperature sensors and the output of the heating element.

A potential design of the dispenser according to an embodiment of the invention and the detection installation thereof provides that the detection installation determines the quantity of liquid previously applied indirectly by way of the air flowing in through the ventilation duct, and displays the determined applied quantity of liquid, or the quantity of liquid remaining in the liquid reservoir calculated from the former, on a display installation. The display installation can be designed as a display, for example an LC display. Depending on the specific application, a simple LED may be sufficient, in particular when the display installation is intended to display only whether the determined applied quantity of liquid corresponds to a predetermined quantity of liquid, or exceeds the predetermined quantity of liquid or is deficient in terms of the predetermined quantity of liquid.

Another design provides that the detection installation is configured for identifying application procedures indirectly by way of the air flowing in through the ventilation duct, wherein it is not required to this end here that the applied quantity of liquid is mandatorily also detected in terms of the quantity of the liquid. Such a design of a detection installation, and the sensor system of the detection installation, are easier to design in technical terms, but are sufficient depending on the field of application.

In a dispenser which for reasons of construction always dispenses doses of liquid of identical size, the information that an application has been performed can thus be sufficient for counting. Such a detection installation in conjunction with an integrated clock can also be configured for comparing planned utilization times and performed application procedures and, in the event of outstanding application procedures at planned utilization times, to emit a preferably acoustic warning signal by way of a signaling installation.

The detection installation described can be integrated directly in an applicator head of a dispenser according to an embodiment of the invention. In the case of single-use dispensers this is however in most instances rather avoided for reasons of ecology and economy. Instead, the disposal in an external module and the disposal in the protective cap, as will yet be explained hereunder, are preferable.

First, for easy disposal of the detection installation in an external detection module, the detection module can be comprised by an embodiment of the invention both in combination with a dispenser (set) to which the detection module is attached, as well as a standalone item.

Such an external detection module can be attached to the housing of the dispenser, preferably in a tool-free manner, and be released from the housing preferably in a tool-free manner. Depending on the specific application, the potential of attaching the detection module only by a tool may however be sufficient. Even when fixedly attached to the dispenser, the module does however not represent an integral part of the dispenser. This means that the module is removable without preventing the functional capability of the dispenser for applying liquid.

The external detection module can be attached to the housing of the dispenser in such a manner that the external detection module sits firmly thereon and is not able to be inadvertently released. Simple handling is advantageous if the external module is to be handled by end-users. In this case, the external module is preferably pushed onto the housing in a force-fitting manner, or secured in a form-fitting manner, in particular by means of threads, against being pulled off.

The detection module is configured for coupling externally to the location of the housing of the dispenser where an introduction opening into the dispenser-proximal part of the ventilation duct is provided.

The detection module can have a measuring duct, and at the end thereof a coupling port, wherein the coupling port is positioned in such a manner that the measuring duct, upon attaching the detection module, is coupled so as to communicate with the introduction opening on the housing of the ventilation duct of the dispenser. An external side of the housing and an internal side of the detection module conjointly preferably delimit an encircling duct to which the introduction opening as well as the coupling port are connected in a communicating manner. The measuring duct, upon coupling, forms part of the ventilation duct.

The detection module preferably but not mandatorily has an annular module housing which surrounds a central recess such that the module housing can be pushed onto the dispenser housing so as to surround the dispenser housing.

The design of the detection installation as part of an external detection module in construction terms is in most instances advantageous in comparison to a solution in which the housing is integrated in the dispenser. This permits the production and/or the use of the dispenser in a design with the detection installation and a design without the detection installation, without the dispenser components which are required for the application of the liquid, and in particular the housing, of the designs having to be specially designed. Moreover, even dispensers which are already commercially available can be retrofitted with a detection module as long as the introduction opening is provided at a location of the housing that is suitable for coupling a detection module.

Furthermore, an external detection module can be removed in a simple, and particularly preferably tool-free, manner from an emptied single-use dispenser, and be placed onto a new dispenser, which is advantageous in terms of economy and ecology. A particular design embodiment of the detection module can therefore be configured having a sensor system in order to register such a dispenser replacement and utilize this information for a reset procedure. For example, a counter can be reset to zero.

As has already been mentioned above, the design of a protective cap having an integrated detection installation is also advantageous. Before this will be discussed in detail, the design of an inventive dispenser according to a second aspect of an embodiment of the invention will first be explained, wherein this design serves in particular as the foundation for the use of a protective cap having a detection installation.

In this second design, a dispenser of the generic type is equipped with a protective cap for covering the applicator opening in the state placed thereon. The protective cap is removed by the user of the dispenser before the dispenser is used, and subsequently replaced. The protective cap can in particular be a plug-fit cap or a screw cap.

The dispenser according to this second aspect of an embodiment of the invention in the ventilation duct has a switch valve which can be opened by activating a push-button provided on the external side of the housing. The ventilation duct is thus closed when the switch valve is not activated. An introduction of air is suppressed. The switch valve is preferably provided in the region of an external surface of the housing of the dispenser such that the switch valve suppresses the ingress of air into the ventilation duct.

In order for the push-button to be activated it is provided that the housing and the protective cap are mutually adapted in such a manner that the protective cap acts on the push-button in the state placed on the housing or when the protective cap is being placed on the housing, thus opening the switch valve. Therefore, the procedure of placing the protective cap, at least in the interim, has the effect of opening the switch valve, thus permitting the inflow of air.

In such a design of the dispenser it is thus not provided that solely the application of liquid, and the negative pressure arising as a result in the liquid reservoir, enables the introduction of air. Instead, the negative pressure is initially maintained, and is optionally even reinforced by activating the dispenser multiple times, and accordingly by a multiple application of liquid. The ventilation can take place only once the protective cap is placed onto the housing again.

This has a plurality of advantages. Independently of the presence of a detection installation, a negative pressure which tends to be more intense, and a greater air flow of the inflowing air caused as a result, can be advantageous, for example in order to release remnants of liquid from a liquid filter at the end of the ventilation duct.

A design embodiment of this type of a dispenser is however particularly advantageous in particular when the dispenser has a detection installation of the type described above. Such a detection installation in terms of the sensor system thereof is easier to design in technical terms when a greater air flow is detected, such as can be achieved by blocking the ventilation duct by the switch valve in the interim.

It is particularly advantageous for the detection installation to be integrated in the protective cap. This results in the advantages which have already been discussed above in the context of the external detection module, in particular the re-usability and the possibility of being able to offer dispensers with and without a detection installation while having a high degree of identical construction.

In the case of the detection installation being integrated in the protective cap, the detection installation is preferably designed as has likewise been described in the context of the external detection module, thus having a measuring duct in or on which the sensor system is provided, and which by placing the protective cap thereon becomes part of the ventilation duct. The activation surface for activating the push-button of the switch valve which is provided on the protective cap is preferably disposed in such a manner that the measuring duct of the protective cap and the ventilation duct in the housing are connected in a communicating manner and so as to be tight in relation to an environment in the transition region, such that the cap-proximal detection installation can directly detect the air flow as soon as the switch valve is opened by the protective cap when the cap is put in place.

The detection of the inflowing air in the context of placing the protective cap can also be advantageous because the detection requires only a brief phase during which the electronics of the detection installation are activated. It is therefore particularly advantageous for the detection installation to possess a switch which is activatable by placing the protective cap on the housing.

The triggering of this switch, which in a detection installation within the housing of the dispenser may also form a common functional unit with the switch valve, activates the detection installation. The detection installation can be deactivated again as soon as the air flow, which is subsequently detected by sensors, is closed off and has been evaluated. Only a small amount of electric power is thus consumed. A battery as part of the detection installation can therefore offer power for the operation of the detection installation over a long time, optionally a plurality of years.

BRIEF DESCRIPTION OF THE DRAWINGS

Further advantages and aspects of the invention are derived from the claims and from the following description of preferred exemplary embodiments of the invention which are explained hereunder by means of the figures in which.

FIGS. 4A and 4B show a second exemplary embodiment of the invention, having an external detection module; and FIGS. 5A and 5B show a third exemplary embodiment of the invention, having a detection module which is integrated in a protective cap.

DETAILED DESCRIPTION OF THE EXEMPLARY EMBODIMENTS

Figures 1, 2A, 2B:
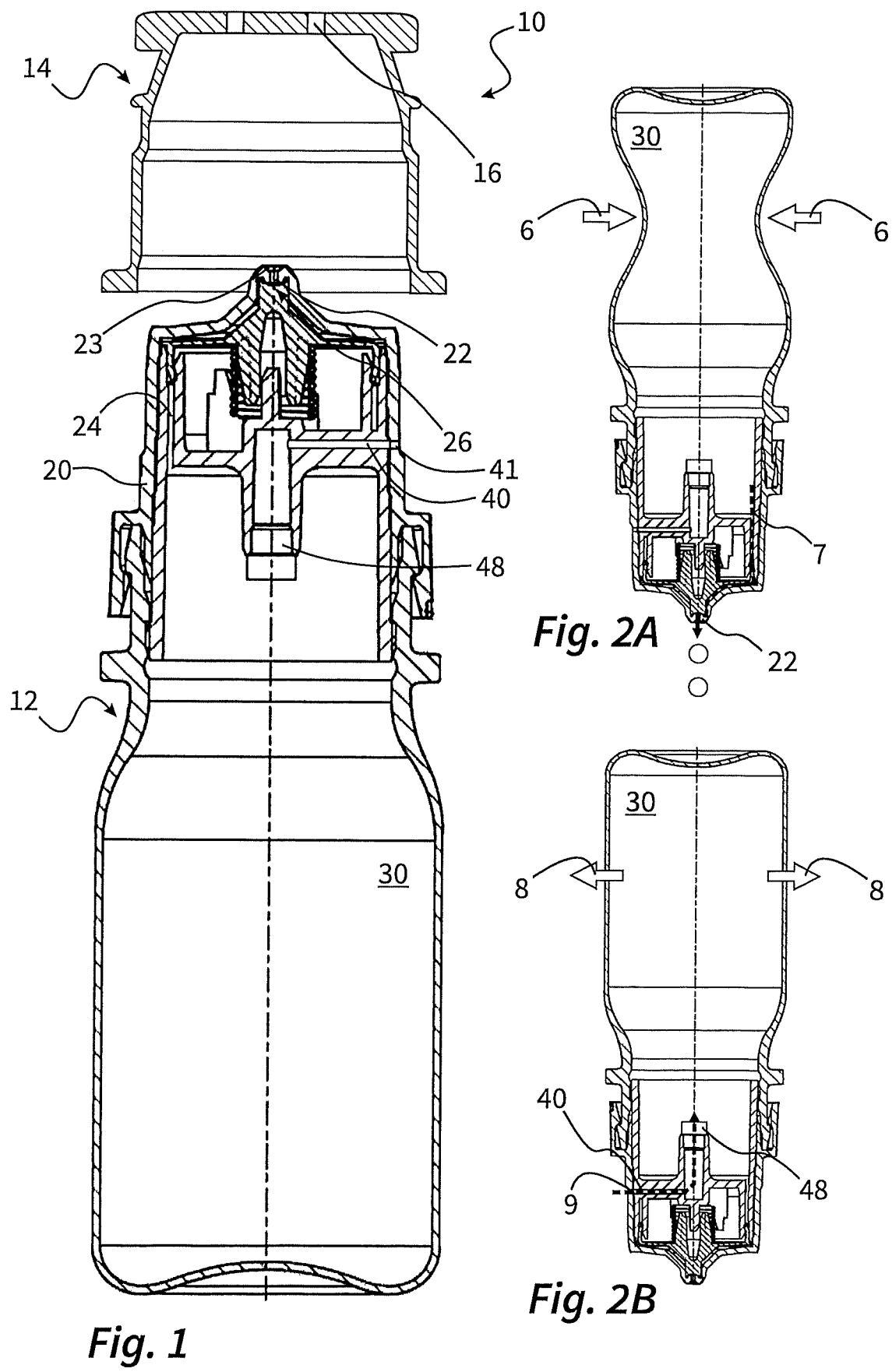
FIGS. 1 and 2A and 2B show a dispenser known per se as a starting point for the designs according to an embodiment of the invention which will be described hereunder and the fundamental functioning mode of this dispenser.

FIGS. 1, 2A and 2B show a liquid dispenser according to the generic type, which in the further course will be refined by modification or addition so as to form a liquid dispenser according to an embodiment of the invention.

The liquid dispenser 10 possesses an applicator device 12 which represents the primary component of the liquid dispenser 10 and in turn possesses a housing 20 which at the distal end is penetrated by an applicator opening 22. In order for this applicator opening 22 to be protected, the dispenser 10 comprises a protective cap 14 which is presently configured as a ventilated protective cap so as to in the placed state allow remnants of liquid remaining on the applicator opening 22 to escape rapidly through ventilation holes 16.

The applicator device 12 possesses a liquid reservoir 30, the walls of the liquid reservoir representing a squeeze bottle, as is yet to be explained hereunder. An applicator head, which apart from the applicator opening 22 already mentioned, includes an applicator duct 24 which connects the liquid reservoir 30 to the applicator opening 22. The applicator head is placed on the liquid reservoir 30. An outlet valve 26, which at a sufficient liquid pressure in a valve chamber opens and thus permits the liquid to exit through the applicator opening 22, is disposed upstream of the applicator opening 22. The dispenser 10 is presently configured as a drop dispenser and beyond the applicator opening 22 possesses a drop-forming surface 23 which externally is delimited by a tear-off edge.

As has already been mentioned, the liquid reservoir 30 is a liquid reservoir 30 configured in the manner of a squeeze bottle. This means that the activation of the dispenser, in the manner highlighted by FIG. 2A, takes place in that the bottle is compressed in the direction of the arrows 6. As a result, a positive pressure is created in the liquid reservoir 30, having the effect that liquid is conveyed along the exit path 7 to the applicator opening 22 and the drop-forming surface 23 and at the drop-forming surface 23 is delivered in the shape of drops. In the absence of the impingement of the squeeze bottle by force, the squeeze bottle re-assumes the initial shape thereof in the manner highlighted by the arrows 8 in FIG. 2B, as a result of which a negative pressure arises in the liquid reservoir 30. This has the effect that air is inducted through a ventilation duct 40, along the ventilation path 9. The inducted air at the end of the ventilation duct 40, in the region of a filter assembly 48, is cleaned of contaminations such as microbes and bacteria. The inflowing air ensures a pressure equalization in the liquid reservoir 30 such that the negative pressure existing in the interim is reduced.

Figure 3:
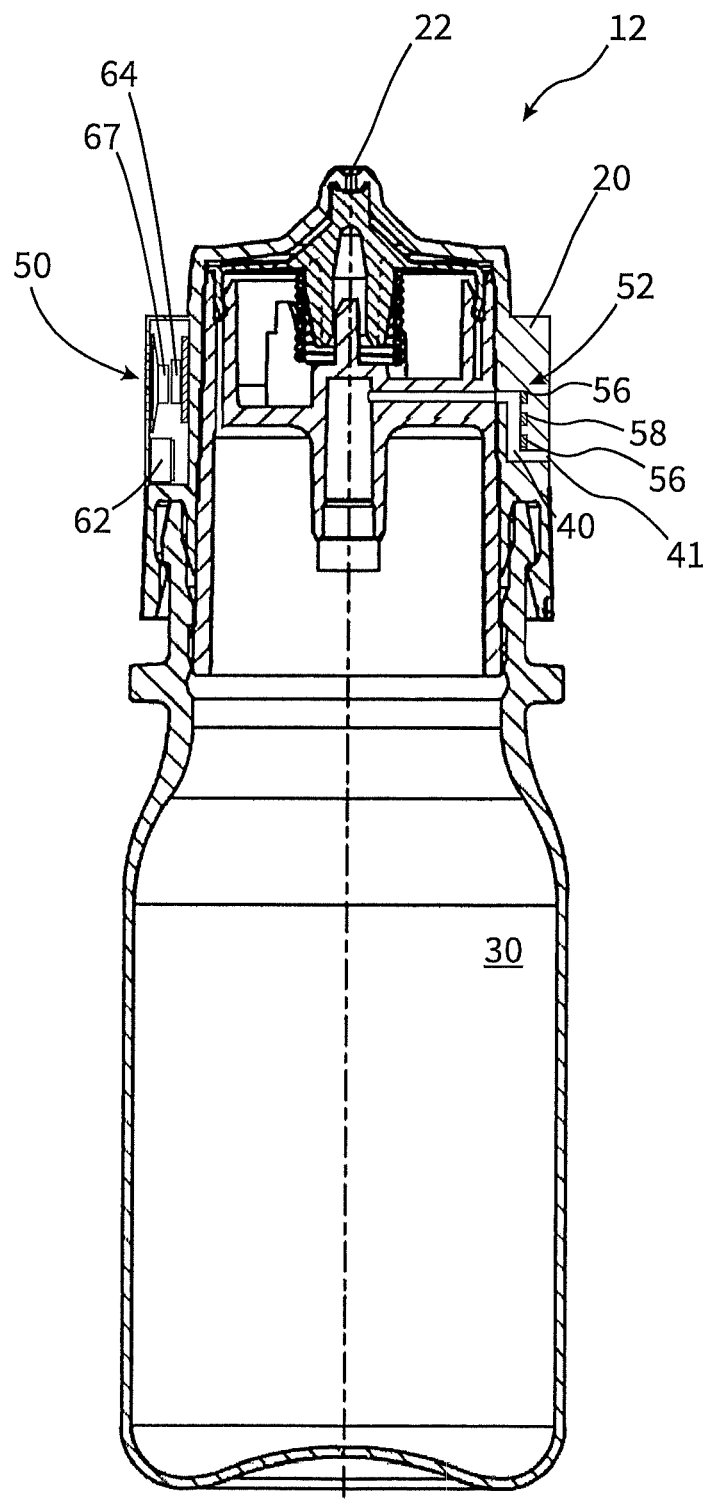
FIG. 3 shows a first exemplary embodiment of the invention, having a detection installation integrated in the dispenser.

FIG. 3 shows a modification of the dispenser of FIG. 1, presently in particular a modification of the applicator device 12. The modification lies in that the housing 20 is of a different type and surrounds a detection installation 50 which is designed for detecting air flowing in through the ventilation duct 40. The detection installation 50 possesses an acoustic signal emitter 67 in the form of a loudspeaker, a microprocessor 64, and an energy source in the form of a battery 62.

The detection installation 50 furthermore possesses a sensor assembly 52 in the ventilation duct 40, the sensor assembly 52 being provided in particular on the wall of the ventilation duct 40. The sensor assembly 52 comprises two temperature sensors 56 and a heating element 58 disposed therebetween. When air now flows through the ventilation duct 40 while air is being inducted according to the phase of FIG. 2B, a temperature of the air ahead of the heating element 58 can thus be detected by the first temperature sensor 56, and the air heated by the heating element 58, in terms of the temperature of the air, can be measured downstream of the heating element 58 by the second temperature sensor 56. The temperature difference is an indicator of whether and how much air has flowed through the ventilation duct 40. A high temperature difference arises at a small air flow. A small temperature difference arises at a large air flow.

The result of the measurements thereof can be evaluated by the microprocessor 64. For example, in the event of an excessively small air flow and consequently an earlier excessively low liquid application, the microprocessor 64 can indicate by way of the loudspeaker 67 that the application has not been performed in an orderly manner. The microprocessor 64, when delivery times have been stored in the memory thereof, can also indicate by way of the loudspeaker 67 that a planned application has not been performed. The user is thus reminded to make up for this application.

The disposal of the sensor assembly 52 in the ventilation duct 40 results in an application being able to be reliably identified without the sensor assembly 52 to this end having to be in direct contact with the liquid.

The fundamental principle in the design embodiment according to FIGS. 4A and 4B is similar to that of FIG. 3. As can be seen in FIG. 4A, the detection installation 50 presently is however designed as part of a detection module 80 which possesses an annular module housing 82 which is provided for being pushed onto the housing 20 of the applicator device 12. FIG. 4B shows the pushed-on state.

The detection module 80 likewise comprises a battery 62 and a microprocessor 64. However, an LC display 66, which enables more complex information to be relayed to the user than is usually the case with a loudspeaker corresponding to FIG. 3, is additionally provided in this design. However, alternatively to the loudspeaker or additionally thereto, a display may also be provided in the design of FIG. 3 and the integration of the detection installation 50 in the housing 20 provided there.

The sensor assembly 52 in the exemplary embodiment of FIGS. 4A and 4B is similar to that of FIG. 3 and is again based on the presence of two temperature sensors 56 and one heating element 58. In this case however, the sensor assembly 52 is not an integral component part of the applicator device 12, in a manner corresponding to FIG. 3, but part of the mentioned detection module 80. With reference to FIG. 4A, a switch 69, only schematically illustrated, is provided on the internal side of the annular module housing 82 of the detection module 80. By means of this switch 69, the detection module 80 can identify when the detection module 80 is being pushed onto the housing 20 of the applicator device 12. This can be utilized for resetting an integrated counter to an initial value, for example. This switch 69 is triggered when the detection module 80 is assembled.

FIG. 4B shows the assembled state. It can be seen here that a coupling port 45 of the measuring duct 44 of the detection module 80 is connected in a communicating manner to an introduction opening 41 of the part of the ventilation duct 40 that is proximal to the applicator device. In order to likewise permit a non-aligned orientation, the housing 20 of the applicator device 12 and the module housing 82 of the detection module 80, when in the coupled state, are configured to define an annular space 84. This permits the detection module to be pushed onto the housing 20 in any arbitrary position.

As has already been mentioned, the sensor assembly 52 is illustrated in the same manner as in the exemplary embodiment of FIG. 3. The presence of the LC display 66 however permits the values detected by way of the sensor assembly 52 to be evaluated to an even greater extent and presented to the user. By detecting the air flow and the duration of the air flow when inducting air through the measuring duct 44 and the ventilation duct 40, it can thus be in particular estimated what quantity of liquid has entered the bottle and consequently what quantity of liquid has previously been applied. Accordingly, the total quantity of already applied liquid can be represented on the LC display 66, or else the quantity of liquid remaining in the liquid reservoir 30, should the initial quantity be known to the detection module 80.

The design embodiment of FIGS. 5A and 5B is similar to that of FIGS. 4A and 4B in terms of the detection installation 50 here also not being an integral component part of the applicator device 12. However, the detection installation 50 in this case is provided in the protective cap 14. This detection installation also possesses a battery 62, a microprocessor 64 and an LC display 66. However, the sensor assembly 52 which is provided on a measuring duct 44 of the cap 14 is presently of a different design, wherein it is fundamentally arbitrary which of the exemplary embodiments is provided with which type of sensor assembly 52. The sensor assembly 52 of FIGS. 5A and 5B possesses a two-part bypass duct 46 which emanates from the measuring duct 44 and in which a membrane 54 is disposed. Depending on the air flow that flows through the measuring duct 44, the membrane 54 is deflected to a variable extent, this being able to be detected by a piezo sensor, for example, and to be further processed by the microprocessor 64.

The protective cap 14 moreover likewise possesses a switch 69 which however has a somewhat different technical significance than the switch 69 in the case of FIGS. 4A and 4B, as is yet to be explained hereunder.

Because the protective cap 14 is obviously not attached to the applicator device 12 during the application of liquid, the applicator device 12 possesses a switch valve 42 which in the state of FIG. 5A covers the introduction opening of the ventilation duct 40 and thus does not permit the introduction of air at this point in time. When the dispenser of FIG. 5A is thus activated as illustrated in FIG. 2A, an application of liquid is indeed performed, but there is no pressure equalization on account of inflowing air. Rather, in the case of a multiple application, an ever-increasing negative pressure is built up in the liquid reservoir 30, the negative pressure not yet able to be equalized at this point of time.

A detection can only take place once the protective cap 14 is placed on the applicator device 12, in the manner highlighted by FIG. 5B. First, the switch 69 is triggered, this resulting in an activation of the detection installation 50. When the cap 14 is depressed as far as the terminal position thereof in FIG. 5B, activation surfaces 15 which are provided in an encircling manner at the lower end of ribs on the protective cap 14 can press onto a push-button 43 of the switch valve 42 and as a result depress the switch valve 42 in the manner highlighted by FIG. 5B. As a result thereof, the ventilation duct 40 is opened, however only once the protective cap 14 has been placed to the extent that air cannot flow in along the lower periphery of the protective cap 14 nor through the ventilation openings on the end face of the cap. This means that the pressure equalization, which at a high negative pressure is rather shock-like, is performed through the measuring duct 44 of the detection installation 50 which has previously been activated by the switch 69 on the cap.

The microprocessor 64 of the detection installation 50 can then display pertinent data on the LC display 66, in particular the overall quantity of liquid applied to date, or else the quantity of liquid still remaining in the liquid reservoir 30. The shock-like pressure equalization is moreover advantageous for separating potential remnants of liquid which remain on the filter assembly 48 from the latter.

As soon as the sensor assembly 52 can no longer detect an air flow in the measuring duct 44, the sensor assembly 52 can change to a power saving mode or completely deactivate itself until the switch 69 is triggered the next time. As a result of the latter, the protective cap 14 can assume the function thereof as a protective cap recording the application over a long time, even in the case of only a small battery 62.

The invention claimed is:

1. A dispenser for applying liquid comprising:
    a housing having an applicator opening for applying liquid;
    a liquid reservoir for storing the liquid prior to the application;
    a ventilation duct by which an ambient atmosphere is connected to the liquid reservoir so as to, after the application of the liquid, permit an inflow of air into the liquid reservoir;
    a protective cap for covering the applicator opening, which is able to be placed on the housing and able to be removed from the housing; and
    a switch valve in the ventilation duct which can be opened by activating a push-button provided on an external side of the housing; and
    wherein the housing and the protective cap are mutually adapted in such a manner that the protective cap acts on the push-button in a state placed on the housing or when the protective cap is being placed on the housing, thus opening the switch valve.

2. The dispenser for applying liquid as claimed in claim 1, further including:
    a detection installation for detecting an application procedure;
    wherein the detection installation is configured for detecting the air flowing in through the ventilation duct.

3. The dispenser for applying liquid as claimed in claim 2, wherein:
    the detection installation is integrated in the protective cap.

4. The dispenser for applying liquid as claimed in claim 2, wherein:
    the detection installation possesses a switch which is activatable by placing the protective cap on the housing.

5. The dispenser for applying liquid as claimed in claim 2, wherein:
    the detection installation is configured for determining the air flow in the ventilation duct as a reaction to the protective cap being put in place.

6. A detection module for a dispenser having a housing including an applicator opening for applying liquid, a liquid reservoir for storing the liquid prior to the application, a ventilation duct by which an ambient atmosphere is connected to the liquid reservoir so as to, after application of the liquid, permit an inflow of air from the ambient atmosphere into the liquid reservoir, the ventilation duct having an introduction opening disposed on an external side of the housing, and a detection installation for detecting an application procedure, the detection installation being configured for detecting the air flowing in through the ventilation duct, wherein:
    the detection module is configured for being externally coupled to the housing of the dispenser;
    the detection module has a measuring duct and is configured for detecting the air flowing through the measuring duct; and
    the measuring duct has a coupling port which, when the detection module is coupled to the housing, is coupled so as to communicate with the introduction opening of the ventilation duct of the dispenser.

7. The detection module as claimed in claim 6, further including:
an annular module housing which surrounds a central recess such that the annular module housing can be pushed onto the dispenser housing so as to surround the dispenser housing.

8. A dispenser set comprising:
a dispenser having a housing and an applicator opening for applying liquid, a liquid reservoir for storing the liquid prior to the application, and a ventilation duct by which an ambient atmosphere is connected to the liquid reservoir so as to, after the application of liquid, permit an inflow of air into the liquid reservoir;
the ventilation duct of the dispenser having an introduction opening on an external side of the housing; and
a detection module configured for being externally coupled to the housing of the dispenser, the ventilation duct of the dispenser having the introduction opening disposed on the external side of the housing;
the detection module having a measuring duct and being configured for detecting the air flowing through the measuring duct; and
the detection module and the housing of the dispenser being mutually adapted in such a manner that a coupling port of the measuring duct of the detection module, when the detection module is coupled to the housing of the dispenser, is coupled so as to communicate with the introduction opening of the ventilation duct of the dispenser.

9. The dispenser set as claimed in claim 8, wherein:
the detection module has a sensor assembly for detecting the air flowing in through the ventilation duct; and wherein:
the sensor assembly is configured for detecting a differential pressure between two locationally spaced apart reference points of the ventilation duct; and/or
the sensor assembly has at least one deflectable surface portion which is deflectable by the air flowing through the ventilation duct; and/or
the sensor assembly comprises at least two temperature sensors and at least one heating element which are disposed in the ventilation duct, wherein the at least two temperature sensors are provided upstream and downstream of the at least one heating element.

10. The dispenser set as claimed in claim 8, wherein:
the detection module is configured for determining a quantity of liquid previously applied indirectly by way of the air flowing in through the ventilation duct; and
the detection module has a display installation and is configured for informing a user about the determined applied quantity of liquid or, calculated therefrom, the quantity of liquid remaining in the liquid reservoir, by way of the display installation.

11. The dispenser set as claimed in claim 8, wherein:
the detection module is configured for identifying application procedures indirectly by way of the air flowing in through the ventilation duct.

12. The dispenser set as claimed in claim 8, wherein:
the dispenser is configured as a squeeze-bottle dispenser and possesses the liquid reservoir, the squeeze-bottle dispenser being manually compressible from an outside thereof for applying the liquid; and/or
the liquid reservoir has a maximum volume between 5 ml and 500 ml; and/or
the dispenser is configured as a drop dispenser and in a region of the applicator opening possesses a drop-forming surface; and/or
the dispenser is configured as a pharmaceutical dispenser and has a liquid reservoir which is filled with a pharmaceutical liquid.

13. The dispenser set as claimed in claim 11, wherein the detection module possesses an internal clock and is configured for comparing planned utilization times and performed application procedures and, in the event of outstanding application procedures at planned utilization times, to emit a warning signal by way of a signaling installation.

14. The dispenser set as claimed in claim 12, wherein the drop-forming surface is externally delimited by a tear-off edge.

15. The dispenser set as claimed in claim 8, wherein the detection module is attached to the housing of the dispenser in a tool-free manner and is releasable from the housing in a tool-free manner.

16. The dispenser set as claimed in claim 15, wherein the detection module possesses a switch activatable by fastening the detection module to the housing.

* * * * *